United States Patent [19]

Fujita et al.

[11] Patent Number: 5,273,955
[45] Date of Patent: Dec. 28, 1993

[54] HERBICIDAL COMPOSITION IN THE FORM OF STABLE SOLUTION OR EMULSIFIABLE CONCENTRATE OF PROPANIL

[75] Inventors: Shigeki Fujita, Yaizu; Kanji Nakamura, Shimizu, both of Japan

[73] Assignee: Kumiai Chemical Industry Co., Ltd., Japan

[21] Appl. No.: 836,506

[22] Filed: Feb. 18, 1992

[30] Foreign Application Priority Data

Feb. 15, 1991 [JP] Japan ................................. 3-42337

[51] Int. Cl.$^5$ ...................... A01N 25/02; A01N 25/30; A01N 37/22
[52] U.S. Cl. ................ 504/339; 71/DIG. 1
[58] Field of Search ................ 71/118, DIG. 1; 504/339

[56] References Cited

U.S. PATENT DOCUMENTS 4,070,178  1/1978  Johnson et al. ................ 71/118
4,400,199  8/1983  Yokoyama et al. .............. 71/94
4,493,726  1/1985  Burdeska et al. ............... 71/118

FOREIGN PATENT DOCUMENTS

18497/76  10/1970  Japan .
59-19084  5/1984  Japan .

*Primary Examiner*—Allen J. Robinson
*Assistant Examiner*—S. Mark Clardy
*Attorney, Agent, or Firm*—Larson and Taylor

[57] ABSTRACT

A herbicide composition containing propanil as active ingredient is now provided in the form of emulsifiable concentrated organic solution of propanil and surface-active agent(s) in non-toxic mixed organic solvents, which is readily dilutable with water to prepare a stable aqueous emulsion comprising the organic solution of propanil as the disperse phase dispersed in water as the continuous phase of the resulting aqueous emulsion without involving precipitation of propanil solids in said emulsion. Said mixed organic solvents may comprise a mixture of a glycol ether-type solvent with either one or two of dimethyl-sulfoxide and N-methyl-2-pyrrolidone, optionally along with an aromatic solvent. Also, a herbicide composition is provided in the form of a stable solution of propanil in non-toxic mixed organic solvents similar to those mentioned above, which is stable on storage and may be formulated into an emulsifiable concentrated organic solution of propanil by adding surface-active agent(s) thereinto.

14 Claims, No Drawings

HERBICIDAL COMPOSITION IN THE FORM OF STABLE SOLUTION OR EMULSIFIABLE CONCENTRATE OF PROPANIL

SUMMARY OF THE INVENTION

This invention relates to a herbicide composition containing propanil as a herbicidally active ingredient and presented in the form of an emulsifiable concentrated organic solution of propanil in non-toxic mixed organic solvents which is stable on storage and may readily be mixed and diluted with water to prepare a stable aqueous emulsion comprising fine liquid particles of the organic solution of propanil as the disperse phase dispersed in water or any other aqueous medium as the continuous phase of said emulsion without involving precipitation or crystallization of propanil into solids in the resulting aqueous emulsion. This aqueous emulsion so prepared may be sprayed to fields of crop plants where weeds undesirable for agriculture, that is, for the cultivation of crop plants are to be controlled or combated. This invention further relates to a herbicide composition containing propanil and presented as a stable solution of propanil in non-toxic mixed organic solvents which is stable on storage in the sense of having no or little tendency to precipitate or crystallize propanil as solids from the solution even at a high content of propanil in the organic solution and which may be formulated into a stably emulsifiable concentrated organic solution of propanil by incorporation of one or more surface-active agents thereinto. Propanil is a conventional herbicidal compound which is known under a chemical name of N-(3,4-dichlorophenyl)propionamide and is little soluble in water.

BACKGROUND OF THE INVENTION

Propanil has been used widely to control or combat the undesirable weeds in the fields of rice plant, especially in the irrigated paddy field of rice plant for many years. Propanil are usually formulated into the forms of wettable powder and emulsifiable concentrated solutions containing propanil which may be mixed and diluted with water before its use and then sprayed for the herbicidal purpose. From experiences in the past, however, it is said that the spraying aqueous emulsions as prepared by dilution of the emulsifiable concentrated organic solutions of propanil with water can ordinarily give better herbicidal effects than those obtainable by spraying the aqueous suspension of propanil as prepared by dilution of the wettable powder of propanil with water, when comparisons are made at the same rate of application of propanil to weeds. Accordingly, the emulsifiable concentrated solutions of propanil have higher practical utilities as the herbicidal agent and have been preferred than the wettable powder of propanil.

Thus, the herbicidal effects obtainable by application of propanil are different, in fact, depending on the difference in the forms of the formulation containing propanil. This difference in the herbicidal effects exerted by different formulations of propanil employed is said to be attributable to the difference in the physical state of propanil which exists in the spraying aqueous emulsion or aqueous suspension of propanil as formed by dilution of the original emulsifiable solution or wettable powder of propanil with water. Namely, the above-mentioned difference in the herbicidal effects obtained by different formulations of propanil employed may be attributable to whether the propanil present in the spraying aqueous emulsion or aqueous suspension after dilution with water is precipitated in crystalline form or amorphous form or is retaining the form of a solution of propanil to a substantial extent. Besides, even when an emulsifiable concentrated solution of propanil in organic solvent(s) is employed and diluted with water to prepare a spraying aqueous emulsion of propanil, the herbicidal effects obtainable by application of said spraying aqueous emulsion cannot be sufficient to achieve the herbicidal purpose, if the emulsified state of the propanil solution as the disperse phase has been destroyed in the resulting aqueous emulsion after dilution with water, resulting in that propanil can precipitate as crystals or as solids form from the water-diluted emulsion as formed. For these reasons, in principle, it is essentially required that an emulsifiable concentrated solution of propanil which is well practicable should show such properties that the fine liquid particles of said concentrated solution resulted as the disperse phase within the aqueous emulsion formed after the dilution with water are stably remaining dispersed in the continuous medium of water without involving precipitation of propanil, either as crystalline or amorphous solids, from the water-diluted emulsion. That is to say, it is required that the well practicable, emulsifiable concentrated solution of propanil should show such nature that this emulsifiable solution of propanil is well dispersible in water and is stable in the sense of having no or little tendency to precipitate or crystallize its propanil component as solid from the aqueous emulsion as formed upon dilution of said emulsifiable concentrated solution of propanil with water. This nature of the emulsifiable concentrated solution of propanil that the latter solution of propanil is dispersible in water and can lead to a stable condition of the emulsion or the stable disperse organic phase in the water medium after the dilution with water but does not involk precipitation of propanil solids is hereinafter referred to as "emulsion stability in water" or merely as "emulsion stability".

Besides, of course, the well practicable, emulsifiable concentrated solution of propanil itself should be highly stable in the sense that it has no or little tendency to precipitate or crystallize its propanil component as solids from said concentrated solution of propanil upon its storage during which it is stored for a long time at room temperature or at lowered temperatures. The stability of the emulsifiable concentrated solution of propanil in the sense just mentioned above is hereinafter referred to as "storage stability".

Furthermore, propanil itself has low solubility in hydrophobic or water-immiscible organic solvents such as aromatic solvents which are conventionally employed in usual, emulsifiable concentrated solutions of certain pesticides. When these water-immiscible organic solvents are used, it is naturally very difficult to prepare an emulsifiable concentrated solution having a high content of propanil. On the other hand, propanil has high solubility in hydrophilic or water-miscible organic solvents such as acetone and cyclohexanone. Therefore, it is easy to prepare an emulsifiable concentrated solution having a high content of propanil when the water-miscible organic solvent is used to dissolve propanil. However, in case when such emulsifiable concentrated solution of propanil in the water-miscible organic solvent is diluted with water, the "emulsion" state of the resulting water-diluted emulsion that the fine liquid particles of the organic solution of propanil are remaining as the dispersed phase in the continuous water medium can be destroyed in short time, as the fine liquid particles of the organic solution of propanil dissolve into the water medium relatively quickly. It is very difficult to prepare any well practicable, emulsifiable concentrated solution of propanil with using the water-miscible organic solvents in which propanil is highly soluble.

Thus, the above-mentioned difficult problems involved in preparation of the stable, emulsifiable concentrated solution of propanil have heretofore been attended by using isophorone, namely 3,5,5-trimethyl-2-cyclohexen-1-one as the organic solvent for dissolution of propanil.

However, as is described in the literature "Inert Ingredients in Pesticide Products: Policy Statement" (Federal Register/Vol. 52, No. 77), isophorone is objectionably toxic as this solvent is included in the class of compounds having strongest toxicity classified by E.P.A. (Environmental Protection Agency). Hence, commercially available emulsifiable concentrated solution of propanil in isophorone can incur the problem of toxicity stemming from isophorone.

Preparation of emulsifiable concentrated solution of propanil without use of isophorone may be achieved by use of cyclohexanone or 4-methylcyclohexanone as a solvent with aid of triethanolamine dodecylbenzenesulfonate as an anionic surfactant along with a nonionic surfactant and in combination with an aromatic solvent (Japanese Patent Application first publication "Kokai" No. 176902/82). Additional incorporation of a polyaromatic compound containing 2 to 5 aromatic rings, for example, dibenzyltoluene has also been proposed (Japanese Patent Application first publication "Kokai" No. 9901/89).

Emulsifiable concentrated solutions of propanil which are prepared using the above-mentioned cyclohexanone, optionally together the organic co-solvents, however, can involve the drawback that solids or crystals of propanil precipitate when such emulsifiable preparations of propanil are diluted in water at 15° C or lower, followed by vigorous stirring and then allowing to stand. Commercial emulsifiable concentrated solutions of propanil in isophorone used as the principal solvent are also accompanied by the drawback that solids or crystals of propanil can often precipitate upon dilution with water.

Emulsifiable concentrated solutions of propanil are usually used in a relatively early stage of spring for the herbicidal purpose, and the temperature of water employed for the dilution is generally low. Further, when the aqueous emulsions as prepared by dilution of the emulsifiable concentrated solutions of propanil with cold water are sprayed, the water-diluted emulsions so prepared need to be repeatedly stirred and allowed to stand in a chemical tank and then, propanil tends to precipitate as solids or crystals from the aqueous emulsions so prepared. The spraying application of such aqueous emulsions containing propanil solids or crystals precipitated, therefore, can lead to insufficient herbicidal effects and also be accompanied by some troubles upon spraying them due to that spray nozzles can clogg by the precipitated propanil solids or crystals.

Other methods for preparation of emulsifiable concentrated solutions of propanil include the use of a ketone, such as methyl n-hexyl ketone, as the solvent for dissolution of propanil (Japanese Patent Application second publication "Kokoku" No. 9275/67). The emulsifiable concentrated solutions of propanil prepared using the ketones are free from the trouble of precipitation of propanil solids or crystals from the water-diluted emulsion and have good "emulsion stability" but can be accompanied by another problemes that, when stored at low temperatures over a long time, solids or crystals of propanil precipitate from its solution and cannot be easily re-dissolved even when allowing to stand at room temperature for a long time.

DETAILED DESCRIPTION OF THE INVENTION

An object of this invention is to overcome these problems of the conventional art and, hence, to provide a new composition presented in the form of an emulsifiable concentrated solution of propanil which does not contain any toxic solvent, which has a good "storage stability" and thus is free from troublesome precipitation of propanil solids or crystals even when stored at room temperature or low temperatures for a long time, and which further shows a good "emulsion stability" in the sense defined hereinbefore in that the present composition can lead to a stably and uniformly emulsified state of the resulting water-diluted emulsion even when the dilution with water is made under actual conditions of use.

Another object of this invention is to provide a composition presented in the form of a stable solution of propanil in a solvent, which does not contain any toxic solvent but can show a good "storage stability" in that, upon its storage at low temperatures for a long time, the precipitation of propanil solids or crystals is not involved from the solution.

In an attempt to overcome the above-described problems of the conventional art, we, the present inventors, have conducted extensive research to prepare emulsifiable concentrated solution of propanil by combined use of a hydrophobic organic solvent with a hydrophilic organic solvent which have ordinarily be utilized in the conventional methods for preparation of usual emulsifiable concentrated solutions of agricultural pesticides other than propanil. However, none of different combinations of organic solvents as ordinarily used in the preparation of conventional emulsifiable concentrated solutions of agricultural pesticides was able to bring about a satisfactory result with respect to preparing the desired well practicable, emulsifiable concentrated solution of propanil.

We, the present inventors, have then proceeded with further intensive research. As a result, we have now found that such a composition comprising propanil and presented in the form of an organic solution of propanil which may be prepared by dissolving propanil in a solvent mixture of a solvent of the glycol ether-type having a solubility of not more than 5% in water at 20° C. with either one of dimethylsulfoxide and N-methyl-2-pyrrolidone is unexpectedly stable as a solution of propanil and hence does not bring about precipitation of propanil solids or crystals from the solution even when said solution is stored at room and low temperatures for a long time. Further, we have found that such emulsifiable concentrated solution of propanil which may be prepared by dissolving propanil in a solvent mixture consisting essentially of the glycol ether-type solvent having a solubility of not more than 5% in water at 20° C. and either one of dimethylsulfoxide and N-methyl-2-pyrrolidone with addition of at least one surfactant thereto has not only an excellent "emulsion stability" to lead to the stably and uniformly emulsified state of the fine liquid particles of the organic solution of propanil as the disperse phase within the water-diluted emulsion as formed by mixing said emulsifiable concentrated solution of propanil with water for dilution, without involving the precipitation of propanil solids, but also shows an excellent "storage stability" to have no or little tendency to precipitate solids or crystals of propanil from the solution even when the latter is a stored at lowered temperatures for long time. Furthermore, we have found that the "storage stability" of the stable, organic solution of propanil in the above solvent mixture, as well as the "emulsion stability" and "storage stability" of the emulsifiable concentrated solution of propanil in the above solvent mixture can be improved further by additional incorporation of an aromatic solvent to the aforesaid solvent mixture. This aromatic solvent is such one which is commonly employed in emulsifiable concentrated solutions of agricultural pesticides. Our above findings have led to the completion of the present invention.

According to a first aspect of the present invention, therefore, there is provided a herbicide composition in the form of a stable solution of propanil, namely N-(3,4-dichlorophenyl)-propionamide as a herbicidally active ingredient dissolved in solvent, wherein the solvent used is either (i) a solvent mixture consisting essentially of such a solvent of the glycol ether-type having a solubility of not more than 5% by weight in water at 20° C. and dimethylsulfoxide or N-methyl-2-pyrrolidone, or (ii) a solvent mixture consisting essentially of the glycol ether-type solvent as defined above, dimethylsulfoxide or N-methyl-2-pyrrolidone and an aromatic solvent.

The herbicide composition according to the first aspect of this invention includes as a preferred embodiment such a stable solution of propanil having such a composition wherein propanil is present in an amount of 10 to 45% by weight, especially 30 to 45% by weight, the glycol ether-type solvent is present in an amount of 35 to 85% by weight, and dimethylsulfoxide or N-methyl-2-pyrrolidone is present in an amount of 1 to 20% by weight, on the basis of the total weight of the composition or solution. With this stable solution of propanil, it has further been found upon our further investigations to be preferred for ensuring the prevention from the precipitation of propanil solids on its storage, that the weight ratio between the glycol ether-type solvent and dimethylsulfoxide or N-methyl-2-pyrrolidone present in the solvent mixture consisting essentially of the glycol ether-type solvent and dimethylsulfoxide or N-methyl-2-pyrrolidone is in a range of 1:0.57 to 1:0.01, preferably 1:0.33 to 1:0.05.

Further, the herbicide composition according to the first aspect of this invention includes as an another preferred embodiment a stable solution of propanil having such a composition wherein propanil is present in an amount of 10 to 45% by weight, especially 30 to 45% by weight, the glycol ether-type solvent is present in an amount of 20 to 85% by weight, dimethylsulfoxide or N-methyl-2-pyrrolidone is present in an amount of 1 to 20% by weight and the aromatic solvent is present in an amount of 5 to 20% by weight, on the basis of the total weight of the composition or solution. With this stable solution of propanil according to the aforesaid another preferred embodiment, it has further been found to be preferred for ensuring the prevention from the precipitation of propanil solids upon its storage, that the weight ratio between the glycol ether-type solvent and dimethylsulfoxide or N-methyl-2-pyrrolidone present in the solvent mixture consisting essentially of the glycol ether-type solvent, dimethylsulfoxide or N-methyl-2-pyrrolidone and the aromatic solvent is in a range of 1:1 to 1:0.01, preferably 1:0.5 to 1:0.05, and said solvent mixture contains the aromatic solvent in a proportion of 5 to 44%, preferably 10 to 30% by weight, based on the total weight of said solvent mixture.

The herbicide composition according to the first aspect of this invention is noticeably advantageous in that it can show a good "storage stability" even when it contains propanil at a high concentration of 30 to 45%, especially 35 to 45% by weight, based on the total weight of the composition or solution.

According to a second aspect of the present invention, there is also provided a herbicide composition in the form of a stably emulsifiable concentrated solution containing propanil as a herbicidally active ingredient dissolved in solvent together with at least one surface active agent, wherein the solvent used is either (i) a solvent mixture consisting essentially of such a solvent of the glycol ether-type having a solubility of not more than 5% by weight in water at 20° C. and dimethylsulfoxide or N-methyl-2-pyrrolidone, or (ii) a solvent mixture consisting essentially of the glycol ether-type solvent as defined above, dimethylsulfoxide or N-methyl-2-pyrrolidone and an aromatic solvent.

The term "emulsifiable concentrated solution" of a pesticide may often simply be termed as "emulsifiable concentrate" of the pesticide.

The herbicide composition according to the second aspect of this invention includes as its one preferred embodiment such a stably emulsifiable concentrated solution of propanil having such a composition wherein propanil is present in an amount of 10 to 45% by weight, especially 30 to 45% by weight, the glycol ether-type solvent is present in an amount of 20 to 85% by weight, and dimethylsulfoxide or N-methyl-2-pyrrolidone is present in an amount of 1 to 20% by weight, and the surface active agent or agents is or are present in an amount of 2 to 15% by weight, on the basis of the total weight of the composition or solution. With this stably emulsifiable concentrated solution of propanil, it has also been found upon our further investigations to be preferred for ensuring the prevention from the precipitation of propanil solids upon its storage or upon its dilution with water, that the weight ratio between the glycol ether-type solvent and dimethylsulfoxide or N-methyl-2-pyrrolidone present in the solvent mixture consisting essentially of the glycol ether-type solvent and dimethylsulfoxide or N-methyl-2-pyrrolidone is in a range of 1:1 to 1:0.01, preferably 1:0.25 to 1:0.05 and wherein the surface active agent or agents may be present in an amount of 2 to 15% by weight on the basis of the total weight of the composition or solution.

The herbicide composition according to the second aspect of this invention includes as its another preferred embodiment such a stably emulsifiable concentrated solution of propanil having such a composition wherein propanil is present in an amount of 10 to 45% by weight, especially 30 to 45% by weight, the glycol ether-type solvent is present in an amount of 20 to 85% by weight, dimethylsulfoxide or N-methyl-2-pyrrolidone is present in an amount of 1 to 20% by weight and the aromatic solvent is present in an amount of 5 to 20% by weight, and the surface active agent or agents is or are present in an amount of 2 to 15% by weight, on the basis of the total weight of the composition or solution. With this stably emulsifiable concentrated solution of propanil, it has also been found to be preferred for ensuring the prevention from the precipitation of propanil solids upon its storage or upon its dilution with water, that the weight ratio between the glycol ether-type solvent and dimethylsulfoxide or N-methyl-2-pyrrolidone present in the solvent mixture consisting essentially of the glycol ether-type solvent, dimethylsulfoxide or N-methyl-2-pyrrolidone and the aromatic solvent is in a range of 1:1 to 1:0.01, preferably 1:0.5 to 1:0.05 and said solvent mixture contains the aromatic solvent in a proportion of 5 to 35%, preferably 10 to 25% by weight, based on the total weight of said solvent mixture, and wherein the surface active agent or agent(s) may be present in an amount of 2 to 15% by weight on the basis of the total weight of the composition.

The herbicide composition according to the second aspect of this invention is noticeably advantageous in that said composition, namely the emulsifiable solution of propanil concerned can show not only a good "storage stability" but also a good "emulsion stability" even when it contains propanil at a high concentration of 30 to 45%, especially 35 to 45% by weight, based on the total weight of the composition or solution. The herbicide compositions, either in the form of solution of propanil, or in the form of a stably emulsifiable concentrated solution of propanil according to the first and second aspects of the present invention, have excellent "storage stability" in that they are free from the defective precipitation of propanil solids or crystals even when they are allowed to stand at a low temperature of $-20°$ C. and have excellent long-term "storage stability". And, the present composition in the form of emulsifiable concentrated solution of propanil shows further excellent "emulsion stability" in that no solids or crystals of propanil precipitate even when it is mixed with water and employed in a form of the emulsion as diluted in water. Further, they are safe herbicide compositions which present no or little toxicity problem, because of the absence of isophorone.

The glycol ether-type solvent commonly usable in the herbicide compositions of this invention is a glycol ether-type solvent which is represented by the following formula (1) or (2):

$$R_1-(O-R_2)_n-OH \quad (1)$$

wherein $R_1$ and $R_2$ individually represent an alkyl group having 5 to 9 carbon atoms or a phenyl group and n represents an integer of 1 to 2, or

$$R_3-O-(R_4-O)_m-R_5 \quad (2)$$

wherein $R_3$, $R_4$ and $R_5$ individually represent an alkyl group having 3 to 5 carbon atoms and m represents an integer of 1 to 2, and which has a solubility of not more than 5% in water at 20° C. Those glycol ethers having a solubility of not more than 1% in water at 20° C. are particularly preferred.

Examples of the glycol ether-type solvents used in the present invention and represented by the formula (1) include, but are not limited to, ethylene glycol monohexyl ether (0.99%), diethylene glycol monohexyl ether (1.7%), ethylene glycol mono-2-ethylhexyl ether (0.2%), diethylene glycol mono-2-ethylhexyl ether (0.3%), ethylene glycol monophenyl ether (2.7%), propylene glycol monophenyl ether (0.2%) and dipropylene glycol monopropyl ether (4.8%). The values (%) given in parentheses represent the solubility (%) of each solvent in water at 20° C.

Illustrative of the glycol ether-type solvents used in the present invention and represented by the formula (2) include, but are not limited to, ethylene glycol dibutyl ether (0.2%) and diethylene glycol dibutyl ether (0.3%). The values (%) given in parentheses represent the solubility (%) of each solvent in water at 20° C.

No particular limitation is imposed on the surfactant or active surface agent usable in the composition of the emulsifiable concentrated solution of propanil according to the second aspect of the present invention, as long as it is suitable for emulsifying and dispersing the emulsifiable concentrated solution of propanil uniformly in water. Usable exemplary surface active agent(s) include nonionic surfactants such as polyoxyethylene alkylether, polyoxyethylene sorbitan alkylate and polyoxyethylene arylphenyl ether; and anionic surfactants such as polyoxyethylene alkylaryl sulfonates, alkyl aryl sulfonates and lignine sulfonates. They can be suitably chosen and employed singly or in combination of two or more, depending on the kind of the glycol ether-type solvent employed.

The herbicide composition in the form of a stable solution of propanil according to the first aspect of this invention may desirably comprise 35 to 45 wt. % of propanil, 35 to 85 wt. % of the glycol ether-type solvent, and 1 to 20 wt. % of dimethylsulfoxide or N-methyl-2-pyrrolidone, based on the total weight of the composition.

On the other hand, the herbicide composition in the form of a stably emulsifiable concentrated solution of propanil according to the second aspect of this invention can desirably comprise 35 to 45 wt. % of propanil, 20 to 85 wt. % of the glycol ether-type solvent, 1 to 20 wt. % of dimethylsulfoxide or N-methyl-2-pyrrolidone, and 10 to 15 wt. % of one or more surface active agent(s), based on the total weight of the composition.

Further, no particular limitation is imposed on the aromatic solvent commonly usable in the herbicide compositions of the present invention. For example, xylene, methylnaphthalene, solvent naphtha, cyclohexane, ethylbenzene, chlorobenzene, dichlorobenzene or the like can be used. The proportion of aromatic solvent may desirably range from 5 wt. % to 20 wt. % based on the total weight (100 wt. %) of the composition, either in the form a solution or in the form of an emulsifiable concentrated solution of propanil.

No particular limitation is imposed on the method for the formulation of the herbicide compositions either in the form of a solution or a stably emulsifiable concentrated solution of propanil according to the present invention, and the compositions may be prepared by conventional technique.

Namely, the herbicide composition in the form of a simple solution or a stably emulsifiable concentrated solution of propanil can be prepared either by weighing propanil and the necessary solvent components separately in predetermined proportions or weighing a pre-prepared solution of propanil in the necessary solvent mixture and the surface active agent(s) separately in predetermined proportions or weighing propanil, the solvent components and the surface active agent(s) separately in predetermined proportions, and placing the respective components into one vessel, followed by stirring them in the vessel under optional heating to dissolve propanil in the mixed solvents with or without the surface active agent(s).

As will be clear from the foregoing descriptions, either the "two-components" solvent mixture (i) consisting of the glycol-ether type solvent and dimethylsulfoxide or N-methyl-2-pyrrolidone, or the "three-components" solvent mixture (ii) consisting of the glycol-ether type solvent, dimethylsulfoxide or N-methyl-2-pyrrolidone and the aromatic solvent may be used and incorporated commonly in the herbicide composition in the form of a stable solution of propanil according to the first aspect of this invention and also in the herbicide composition in the form of a stably emulsifiable concentrated solution of propanil according to the second aspect of this invention. From our further another investigations, however, we have now found that, in place of the "two-components" solvent mixture (i) or the "three-components" solvent mixture (ii) as defined hereinbefore, there may equally be utilized either (iii) such a "three-components" solvent mixture consisting of the glycol-ether type solvent, dimethylsulfoxide and N-methyl-2-pyrrolidone, or (iv) such a "four-components" solvent mixture consisting of the glycolether type solvent, dimethylsulfoxide, N-methyl-2-pyrrolidone and the aromatic solvent for the purposes to dissolve propanil and prepare a stable solution of propanil or a stably emulsifiable concentrated solution of propanil having satisfactory properties, including the good "storage stability" and good "emulsion stability" as intended by the present invention. Besides, it has been found that, for the here intended purposes, the natures and proportions of the respective particular solvent components present in the above-mentioned "three-components" solvent mixture (iii) and in the above-mentioned "four-components" solvent mixture (iv) may suitably be similar to or the same as those set forth hereinbefore in respect of the aforesaid "two-components" solvent mixture (i) and the aforesaid "three-components" solvent mixture (ii) which are usuable according to the first and second aspects of this invention. This similarly applies to the nature and proportion of the available surface active agent(s).

According to the third aspect of this invention, therefore, there is provided a herbicide composition in the form of a stable solution of propanil as a herbicidally active ingredient dissolved in solvent, wherein the solvent used is either (iii) a solvent mixture consisting essentially of such a solvent of the glycol ether-type having a solubility of not more than 5% by weight in water at 20° C., dimethylsulfoxide and N-methyl-2-pyrrolidone, or (iv) a solvent mixture consisting essentially of the glycol ether-type solvent as defined above, dimethylsulfoxide, N-methyl-2-pyrrolidone, and an aromatic solvent.

A preferred formulation of the herbicide composition according to the third aspect of this invention may be a stable solution of propanil wherein propanil is present in an amount of 10 to 45% by weight, especially 30 to 45% by weight, the glycol ether-type solvent is present in amount of 20 to 85% by weight, both of dimethylsulfoxide and N-methyl-2-pyrrolidone are totally present in an amount of 1 to 20% by weight and, if desired, the aromatic solvent is further present in an amount of 5 to 20% by weight, on the basis of the total weight of the composition, and wherein the weight ratio between the glycol ether-type solvent and the combination of dimethylsulfoxide with N-methyl-2-pyrrolidone may preferably be in a range of 1:0.57 to 1:0.01 in the presence of the aromatic solvent but be in a range of 1:1 to 1:0.01 in the absence of the aromatic solvent.

According to the fourth aspect of this invention, there is provided a herbicide composition presented in the form of a stably emulsifiable concentrated solution containing propanil as a herbicidally active ingredient dissolved in solvent together with at least one surface active agent, wherein the solvent used is either (iii) a solvent mixture consisting essentially of such a solvent of the glycol ether-type having a solubility of not more than 5% by weight in water at 20° C., diemthylsulfoxide and N-methyl-2-pyrrolidone, or (iv) a solvent mixture consisting essentially of the glycol ether-type solvent as defined above, dimethylsulfoxide, N-methyl-2-pyrrolidone and an aromatic solvent.

A preferred formulation of the herbicide composition according to the fourth aspect of this invention may be an emulsifiable concentrated solution of propanil wherein propanil is present in an amount of 10 to 45% by weight, especially 30 to 45% by weight, the glycol ether-type solvent is present in an amount of 20 to 85% by weight, both of dimethylsulfoxide and N-methyl-2-pyrrolidone are totally present in an amount of 1 to 20% by weight, and the surface active agent or agents is or are present in an amount of 2 to 15% by weight and, if desired, the aromatic solvent is further present in an amount of 5 to 20% by weight, on the basis of the total weight of the composition, and wherein the weight ratio between the glycol ether-type solvent and the combination of dimethylsulfoxide with N-methyl-2-pyrrolidone may preferably be in a range of 1: 1 to 1:0.01.

According to the fifth and most generic aspect of this invention, there is provided a herbicide composition presented in the form of a stably emulsifiable concentrated solution containing propanil as a herbicidally active ingredient dissolved in solvent together with at least one surface active agent, wherein the solvent used is either (i) a solvent mixture consisting essentially of such a solvent of the glycol ether-type having a solubility of not more than 5% by weight in water at 20° C. and dimethylsulfoxide or N-methyl-2-pyrrolidone, or (ii) a solvent mixture consisting essentially of the glycol ether-type solvent as defined above, dimethylsulfoxide or N-methyl-2-pyrrolidone and an aromatic solvent, or (iii) a solvent mixture consisting essentially of such a solvent of the glycol ether-type as defined above, dimethylsulfoxide and N-methyl-2-pyrrolidone, or (iv) a solvent mixture consisting essentially of the glycol ether-type solvent as defined above, dimethylsulfoxide, N-methyl-2-pyrrolidone and an aromatic solvent.

A preferred formulation of the herbicide composition according to the fifth aspect of this invention include a stably emulsifiable concentrated solution of propanil wherein propanil is present in an amount of 10 to 45% by weight, especially 30 to 45% by weight, the glycol ether-type solvent is present in an amount of 20 to 85% by weight, and dimethylsulfoxide or N-methyl-2-pyrrolidone or both is or are totally present in an amount of 1 to 20% by weight, the surface active agent or agents is or are present in an amount of 2 to 15% by weight and, if desired, the aromatic solvent is further present in an amount of 5 to 20% by weight, on the basis of the total weight of the composition. Here, the weight ratio between the glycol ether-type solvent and dimethylsulfoxide or N-methyl-2-pyrrolidone or the combination of the latter two may again preferably be in a range of 1:1 to 1:0.01 similarly to the second aspect composition of this invention.

The present invention will hereinafter be illustrated with reference to the following Examples and Comparative Examples, in which all designations of "%" mean "% by weight".

Exemplary formulations of Examples 1, 2, and 11-27 are illustrative of particular examples of a stable solution of propanil according to the first aspect of this invention; exemplary formulations of Examples 3-9 and 29-45 are illustrative of particular examples of a stably emulsifiable concentrated solution of propanil according to the second aspect of this invention, exemplary formulation of Example 10 is illustrative of one example of the stable solution of propanil according to the third aspect of this invention; and exemplary formulation of Example 28 is illustrative of one example of the stably emulsifiable concentrated solution of propanil according to the fourth aspect of this invention. Thus, Examples 1 to 45 as a whole are illustrative of the most generic, fifth aspect of this invention.

EXAMPLE 1

A predetermined amount of propanil was added and dissolved under stirring in predetermined amounts of solvents, to prepare a composition in the form of a solution of propanil and having the following formulation:

| | |
|---|---|
| Propanil | 35% |
| Diethylene glycol mono-2-ethylhexyl ether | 60% |
| Dimethylsulfoxide | 5% |

In a manner similar to Example 1, compositions in the form of a solution of propanil of Example 2 and Comparative Examples 1 to 2 were prepared.

EXAMPLE 2

| | |
|---|---|
| Propanil | 35% |
| Ethylene glycol monohexyl ether | 55% |
| N-Methyl-2-pyrrolidone | 10% |

COMPARATIVE EXAMPLE 1

| | |
|---|---|
| Propanil | 35% |
| Ethylene glycol mono-2-ethylhexyl ether | 65% |

COMPARATIVE EXAMPLE 2

| | |
|---|---|
| Propanil | 35% |
| Ethylene glycol monohexyl ether | 65% |

EXAMPLE 3

Predetermined amounts of propanil, solvents and surfactants were stirred together under optional heating to mix them, and to prepare compositions in the form of an emulsifiable concentrated solution of propanil and having the following formulation:

| | |
|---|---|
| Propanil | 35% |
| Diethylene glycol mono-2-ethylhexyl ether | 52% |
| Dimethylsulfoxide | 5% |
| Mixture of polyoxyalkylene arylphenyl ether and alkyl benzene sulfonate ("New Cargen ST-60", trade name; surfactant of Takemoto Oil & Fat Co., Ltd.) | 8% |

In a manner similar to Example 3, compositions in the form of an emulsifiable concentrated solution of propanil of Examples 4 to 8 and Comparative Examples 3 to 16 were prepared.

EXAMPLE 4

| | |
|---|---|
| Propanil | 35% |
| Diethylene glycol mono-2-ethylhexyl ether | 37% |
| Dimethylsulfoxide | 5% |
| Xylene | 15% |
| Mixture of polyoxyalkylene arylphenyl ether and alkyl benzene sulfonate ("New Cargen ST-60", trade name; surfactant of Takemoto Oil & Fat Co., Ltd.) | 8% |

EXAMPLE 5

| | |
|---|---|
| Propanil | 35% |
| Ethylene glycol monohexyl ether | 45% |
| N-Methyl-2-pyrrolidone | 10% |
| Mixture of polyoxyalkylene arylphenyl ether and alkyl benzene sulfonate ("New Cargen ST-60", trade name; surfactant of Takemoto Oil & Fat Co., Ltd.) | 7% |
| Mixture of polyoxyethylene arylphenyl ether formaldehyde condensation product, polyoxyalkylene arylphenyl ether, alkyl benzene sulfonate and xylene ("New Cargen ST-40", trade name; surfactant of Takemoto Oil & Fat Co., Ltd.) | 3% |

EXAMPLE 6

| | |
|---|---|
| Propanil | 15% |
| Ethylene glycol monohexyl ether | 35% |
| N-Methyl-2-pyrrolidone | 10% |
| Methylnaphthalene | 10% |
| Mixture of polyoxyalkylene arylphenyl ether and alkyl benzene sulfonate ("New Cargen ST-60", trade name; surfactant of Takemoto Oil & Fat Co., Ltd.) | 7% |
| Mixture of polyoxyethylene arylphenyl ether-formaldehyde condensation product, polyoxyalkylene arylphenyl ether, alkyl benzene sulfonate and xylene ("New Cargen ST-40", trade name; surfactant of Takemoto Oil & Fat Co., Ltd.) | 3% |

EXAMPLE 7

| | |
|---|---|
| Propanil | 45% |
| Diethylene glycol dibutyl ether | 35% |
| N-Methyl-2-pyrrolidone | 15% |
| Mixture of polyoxyalkylene arylphenyl ether and alkyl benzene sulfonate ("New Cargen ST-60", trade name; surfactant of Takemoto Oil & Fat Co., Ltd.) | 4% |
| Polyoxyethylene alkylphenyl ether sulfonate ("Hitenor", trade mark; surfactant of Daiichi Kogyo Seiyaku Co., Ltd.) | 1% |

EXAMPLE 8

| | |
|---|---|
| Propanil | 10% |
| Ethylene glycol monophenyl ether | 75% |
| Dimethylsulfoxide | 5% |
| Mixture of polyoxyalkylene arylphenyl ether and alkyl benzene sulfonate ("New Cargen ST-60", trade name; surfactant of Takemoto Oil & Fat Co., Ltd.) | 8% |

-continued

| Mixture of polyoxyethylene styrylphenyl ether and alkyl benzene sulfonate ("Solpole 3313B", trade name; surfactant of Toho Chemical Industry Co., Ltd.) | 2% |

EXAMPLE 9

| Propanil | 35% |
| Ethylene glycol mono-2-ethylhexyl ether | 37% |
| Dimethylsulfoxide | 5% |
| Xylene | 15% |
| Mixture of polyoxyalkylene arylphenyl ether and alkyl benzene sulfonate ("New Cargen ST-60", trade name; surfactant of Takemoto Oil & Fat co., Ltd.) | 8% |

COMPARATIVE EXAMPLE 3

| Propanil | 35% |
| Diethylene glycol mono-2-ethylhexyl ether | 57% |
| Mixture of polyoxyalkylene arylphenyl ether and alkyl benzene sulfonate ("New Cargen ST-60", trade name; surfactant of Takemoto Oil & Fat Co., Ltd.) | 8% |

COMPARATIVE EXAMPLE 4

| Propanil | 35% |
| Dimethylsulfoxide | 57% |
| Mixture of polyoxyalkylene arylphenyl ether and alkyl benzene sulfonate ("New Cargen ST-60", trade name; surfactant of Takemoto Oil & Fat Co., Ltd.) | 8% |

COMPARATIVE EXAMPLE 5

| Propanil | 35% |
| Dimethylsulfoxide | 5% |
| Xylene | 52% |
| Mixture of polyoxyethylene styrylphenyl ether, polyoxyethylene fatty acid derivative and Xylene ("Solpole HYX", trade name; surfactant of Toho Chemical Industry Co., Ltd.) | 8% |

COMPARATIVE EXAMPLE 6

| Propanil | 35% |
| Diethylene glycol moho-2-ethylhexyl ether | 52% |
| N,N-dimethylformamide | 5% |
| Mixture of polyoxyalkylene arylphenyl ether and alkyl benzene sulfonate ("New Cargen ST-60", trade name; surfactant of Takemoto Oil & Fat Co., Ltd.) | 8% |

COMPARATIVE EXAMPLE 7

| Propanil | 35% |
| Diethylene glycol mono-2-ethylhexyl ether | 42% |
| Xylene | 15% |
| Mixture of polyoxyalkylene arylphenyl ether and alkyl benzene sulfonate ("New Cargen ST-60", trade name; surfactant of Takemoto Oil & Fat Co., Ltd.) | 8% |

COMPARATIVE EXAMPLE 8

| Propanil | 35% |
| Ethylene glycol diethyl ether* | 37% |
| Dimethylsulfoxide | 5% |
| Xylene | 15% |
| Mixture of polyoxyalkylene arylphenyl ether and alkyl benzene sulfonate ("New Cargen ST-60", trade name; surfactant of Takemoto Oil & Fat Co., Ltd.) | 8% |

(*solubility in water at 20° C.: 21.0%)

COMPARATIVE EXAMPLE 9

| Propanil | 35% |
| Ethylene glycol monohexyl ether | 55% |
| Mixture of polyoxyethylene arylphenyl ether-formaldehyde condensation product, polyoxyalkylene arylphenyl ether, alkyl benzene sulfonate and xylene ("New Cargen ST-50", trade name; surfactant of Takemoto Oil & Fat Co., Ltd.) | 6% |
| Mixture of polyoxyethlene arylphenyl ether-formaldehyde condenstaion product, polyoxyalkylene arylphenyl ether, alkyl benzene sulfonate and xylene ("New Cargen ST-30", trade name; surfactant of Takemoto Oil & Fat Co., Ltd.) | 4% |

COMPARATIVE EXAMPLE 10

| Propanil | 35% |
| N-Methyl-2-pyrrolidone | 55% |
| Mixture of polyoxyethylene alkylaryl ether and alkyl aryl sulfonate ("Agrisol H-172", trade name; surfactant of Kao Corporation) | 10% |

COMPARATIVE EXAMPLE 11

| Propanil | 35% |
| N-Methyl-2-pyrrolidone | 10% |
| Methylnaphthalene | 45% |
| Mixture of polyoxyethylene styrylphenyl ether, polyoxyethylen styrylphenyl ether polymer, alkyl aryl sulfonate and xylene ("Solpole SNX", trade name; surfactant of Toho Chemical Industry Co., Ltd.) | 10% |

COMPARATIVE EXAMPLE 12

| Propanil | 35% |
| Ethylene glycol monohexyl ether | 45% |
| n-Propyl alcohol | 10% |
| Mixture of polyoxyethylene arylphenyl ether-formaldehyde condensation product, polyoxyalkylene arylphenyl ether, alkyl benzene sulfonate and xylene ("New Cargen ST-50", trade name; surfactant of Takemoto Oil & Fat Co., Ltd.) | 6% |
| Mixture of polyoxyethylene arylphenyl ether-formaldehyde condensation product, polyoxyalkylene arylphenyl ether, alkyl benzene sulfonate and xylene ("New Cargen ST-30", trade name; surfactant of Takemoto Oil & Fat Co., Ltd.) | 4% |

COMPARATIVE EXAMPLE 13

| | |
|---|---|
| Propanil | 35% |
| Ethylene glycol monohexyl ether | 45% |
| Methylnaphthalene | 10% |
| Mixture of polyoxyethylene arylphenyl ether-formaldehyde cohdensation product, polyoxyalkylene arylphenyl ether, alkyl benzene sulfonate and xylene ("New Cargen ST-50", trade name; surfactant of Takemoto Oil & Fat Co., Ltd.) | 6% |
| Mixture of polyoxyethylene arylphenyl ether-formaldehyde condensation product, polyoxyalkylene arylphenyl ether, alkyl benzene sulfonate and xylene ("New Cargen ST-30", trade name; surfactant of Takemoto Oil & Fat Co., Ltd.) | 4% |

COMPARATIVE EXAMPLE 14

| | |
|---|---|
| Propanil | 35% |
| Cyclohexanone | 38% |
| Triethanolamine dodecylbenzenesulfonate | 8% |
| Xylene | 7% |
| Mixture of polyoxyethylene nonylphenyl ether, alkyl benzene sulfonate and xylene ("Sanimal", trade mark; surfactant of Japan Surfactant Co., Ltd.) | 12% |

COMPARATIVE EXAMPLE 15

| | |
|---|---|
| Propanil | 35% |
| Methyl n-hexyl ketone | 40% |
| Xylene | 10% |
| Mixture of polyoxyethylene-modified aryl phenyl ether, polyoxthylene phenyl ether, alkyl aryl sulfonate and xylene ("New Cargen KK-V", trade name; surfactant of Takemoto Oil & Fat Co., Ltd.) | 15% |

COMPARATIVE EXAMPLE 16

| | |
|---|---|
| Propanil | 35% |
| Isophorone | 30% |
| Xylene | 25% |
| Mixture of polyoxyethyene alkylaryl ether and alkyl aryl sulfonate ("Agrisol H-172", trade name; surfactant of Kao Corporation) | 10% |

In a manner similar to Example 1, compositions in the form of a solution of propanil of Examples 10 to 27 were prepared.

EXAMPLE 10

| | |
|---|---|
| Propanil | 35% |
| Ethylene glycol monohexyl ether | 55% |
| Dimethylsulfoxide | 5% |
| N-methyl-2-pyrrolidone | 5% |

EXAMPLE 11

| | |
|---|---|
| Propanil | 10% |
| Diethylene glycol mono-2-ethylhexyl ether | 85% |
| Dimethylsulfoxide | 5% |

EXAMPLE 12

| | |
|---|---|
| Propanil | 14% |
| Diethylene glycol mono-2-ethylhexyl ether | 85% |
| Dimethylsulfoxide | 1% |

EXAMPLE 13

| | |
|---|---|
| Propanil | 45% |
| Diethylene glycol mono-2-ethylhexyl ether | 35% |
| Dimethylsulfoxide | 20% |

EXAMPLE 14

| | |
|---|---|
| Propanil | 35% |
| Diethylene glycol mono-2-ethylhexyl ether | 45% |
| Dimethylsulfoxide | 5% |
| Xylene | 15% |

EXAMPLE 15

| | |
|---|---|
| Propanil | 35% |
| Diethylene glycol monohexyl ether | 60% |
| Dimethylsulfoxide | 5% |

EXAMPLE 16

| | |
|---|---|
| Propanil | 35% |
| Ethylene glycol mono-2-ethyhexyl ether | 60% |
| Dimethylsulfoxide | 5% |

EXAMPLE 17

| | |
|---|---|
| Propanil | 35% |
| Ethylene glycol monophexyl ether | 60% |
| Dimethylsulfoxide | 5% |

EXAMPLE 18

| | |
|---|---|
| Propanil | 35% |
| Propylene glycol monophenyl ether | 60% |
| Dimethylsulfoxide | 5% |

EXAMPLE 19

| | |
|---|---|
| Propanil | 35% |
| Dipropylene glycol monopropyl ether | 60% |
| Dimethylsulfoxide | 5% |

EXAMPLE 20

| | |
|---|---|
| Propanil | 35% |
| Ethylene glycol dibutyl ether | 60% |
| Dimethylsulfoxide | 5% |

EXAMPLE 21

| Propanil | 35% |
|---|---|
| Diethylene glycol dibutyl ether | 60% |
| Dimethylsulfoxide | 5% |

EXAMPLE 22

| Propanil | 35% |
|---|---|
| Diethylene glycol mono-2-ethylhexyl ether | 45% |
| Dimethylsulfoxide | 5% |
| Methylnaphthalene | 15% |

EXAMPLE 23

| Propanil | 35% |
|---|---|
| Diethylene glycol mono-2-ethylhexyl ether | 45% |
| Dimethylsulfoxide | 5% |
| Solvent naphtha | 15% |

EXAMPLE 24

| Propanil | 35% |
|---|---|
| Diethylene glycol mono-2-ethylhexyl ether | 45% |
| Dimethylsulfoxide | 5% |
| Cyclohexane | 15% |

EXAMPLE 25

| Propanil | 35% |
|---|---|
| Diethylene glycol mono-2-ethylhexyl ether | 45% |
| Dimethylsulfoxide | 5% |
| Ethylbenzene | 15% |

EXAMPLE 26

| Propanil | 35% |
|---|---|
| Diethylene glycol mono-2-ethylhexyl ether | 45% |
| Dimethylsulfoxide | 5% |
| Chlorobenzene | 15% |

EXAMPLE 27

| Propanil | 35% |
|---|---|
| Diethylene glycol mono-2-ethylhexyl ether | 45% |
| Dimethylsulfoxide | 5% |
| Dichlorobenzene | 15% |

In a manner similar to Example 3, compositions in the form of a stably emulsifiable concentrated solution of propanil of Examples 28 to 45 and Comparative Examples 17 to 19 were obtained.

EXAMPLE 28

| Propanil | 35% |
|---|---|
| Ethylene glycol monohexyl ether | 45% |
| N-Methyl-2-pyrrolidone | 5% |
| Dimethylsulfoxide | 5% |
| Mixture of polyoxyalkylene arylphenyl ether and alkyl benzene sulfonate ("New Cargen ST-60", trade name; surfactant) | 7% |
| Mixture of polyoxyethylene arylphenyl ether-formaldehyde condensation product, polyoxyalkylene arylphenyl ether, alkyl benzene sulfonate and xylene ("New Cargen ST-40", trade name; surfactant) | 3% |

EXAMPLE 29

| Propanil | 10% |
|---|---|
| Diethylene glycol mono-2-ethylhexyl ether | 85% |
| Dimethylsulfoxide | 1% |
| Mixture of polyoxyalkylene arylphenyl ether and alkyl benzene sulfonate ("New Cargen ST-60", trade name; surfactant) | 4% |

EXAMPLE 30

| Propanil | 45% |
|---|---|
| Diethylene glycol mono-2-ethylhexyl ether | 39% |
| Dimethylsulfoxide | 1% |
| Mixture of polyoxyalkylene arylphenyl ether and alkyl benzene sulfonate ("New Cargen ST-60", trade name; surfactant) | 15% |

EXAMPLE 31

| Propanil | 45% |
|---|---|
| Diethylene glycol mono-2-ethylhexyl ether | 20% |
| Dimethylsulfoxide | 20% |
| Mixture of polyoxyalkylene arylphenyl ether and alkyl benzene sulfonate ("New Cargen ST-60", trade name; surfactant) | 15% |

EXAMPLE 32

| Propanil | 10% |
|---|---|
| Diethylene glycol mono-2-ethylhexyl ether | 82% |
| Dimethylsulfoxide | 1% |
| Xylene | 5% |
| Mixture of plyoxyalkylene arylphenyl ether and alkyl benzene sulfonate ("New Cargen ST-60", trade name; surfactant) | 2% |

EXAMPLE 33

| Propanil | 30% |
|---|---|
| Diethylene glycol mono-2-ethylhexyl ether | 20% |
| Dimethylsulfoxide | 20% |
| Xylene | 20% |
| Mixture of polyoxyalkylene arylphenyl ether and alkyl benzene sulfonate ("New Cargen ST-60", trade name; surfactant) | 10% |

EXAMPLE 34

| Propanil | 45% |
|---|---|
| Diethylene glycol mono-2-ethylhexyl ether | 20% |
| Dimethylsulfoxide | 20% |
| Xylene | 5% |
| Mixture of polyoxyalkylene arylphenyl ether and alkyl benzene sulfonate ("New Cargen ST-60", trade name; surfactant) | 10% |

EXAMPLE 35

| | |
|---|---|
| Propanil | 35% |
| Diethylene glycol monohexyl ether | 52% |
| Dimethylsulfoxide | 5% |
| Mixture of polyoxyalkylene arylphenyl ether and alkyl benzene sulfonate ("New Cargen ST-60", trade name; surfactant) | 8% |

EXAMPLE 36

| | |
|---|---|
| Propanil | 35% |
| Ethylene glycol mono-2-ethyhexyl ether | 52% |
| Dimethylsulfoxide | 5% |
| Mixture of polyoxyalkylene arylphenyl ether and alkyl benzene sulfonate ("New Cargen ST-60", trade name; surfactant) | 8% |

EXAMPLE 37

| | |
|---|---|
| Propanil | 35% |
| Propylene glycol monophenyl ether | 52% |
| Dimethylsulfoxide | 5% |
| Mixture of polyoxyalkylene arylphenyl ether and alkyl benzene sulfonate ("New Cargen ST-60", trade name surfactant) | 8% |

EXAMPLE 38

| | |
|---|---|
| Propanil | 35% |
| Dipropylene glycol monopropyl ether | 52% |
| Dimethylsulfoxide | 5% |
| Mixture of polyoxyalkylene arylphenyl ether and alkyl benzene sulfonate ("New Cargen ST-60", trade name; surfactant) | 8% |

EXAMPLE 39

| | |
|---|---|
| Propanil | 35% |
| Ethylene glycol dibutyl ether | 52% |
| Dimethylsulfoxide | 5% |
| Mixture of polyoxyalkylene arylphenyl ether and alkyl benzene sulfonate ("New Cargen ST-60", trade name; surfactant) | 8% |

EXAMPLE 40

| | |
|---|---|
| Propanil | 35% |
| Diethylene glycol dibutyl ether | 52% |
| Dimethylsulfoxide | 5% |
| Mixture of polyoxyalkylene arylphenyl ether and alkyl benzene sulfonate ("New Cargen ST-60", trade name; surfactant) | 8% |

EXAMPLE 41

| | |
|---|---|
| Propanil | 35% |
| Diethylene glycol moo-2-ethylhexyl ether | 37% |
| Dimethylsulfoxide | 5% |
| Solvent naphtha | 15% |
| Mixture of polyoxyalkylene arylphenyl ether and alkyl benzene sulfonate ("New Cargen ST-60", trade name; surfactant) | 8% |

EXAMPLE 42

| | |
|---|---|
| Propanil | 35% |
| Diethylene glycol mono-2-ethylhexyl ether | 37% |
| Dimethylsulfoxide | 5% |
| Cyclohexane | 15% |
| Mixture of polyoxyalkylene arylphenyl ether and alkyl benzene sulfonate ("New Cargen ST-60", trade name; surfactant) | 8% |

EXAMPLE 43

| | |
|---|---|
| Propanil | 35% |
| Diethylene glycol mono-2-ethylhexyl ether | 37% |
| Dimethylsulfoxide | 5% |
| Ethylbenzene | 15% |
| Mixture of polyoxyalkylene arylphenyl ether and alkyl benzene sulfonate ("New Cargen ST-60", trade name; surfactant) | 8% |

EXAMPLE 44

| | |
|---|---|
| Propanil | 35% |
| Diethylene glycol mono-2-ethylhexyl ether | 37% |
| Dimethylsulfoxide | 5% |
| Chlorobenzene | 15% |
| Mixture of polyoxyalkylene arylphenyl ether and alkyl benzene sulfonate ("New Cargen ST-60", trade name; surfactant) | 8% |

EXAMPLE 45

| | |
|---|---|
| Propanil | 35% |
| Diethylene glycol mono-2-ethylhexyl ether | 37% |
| Dimethylsulfoxide | 5% |
| Dichlobenzene | 15% |
| Mixture of polyoxyalkylene arylphenyl ether and alkyl benzene sulfonate ("New Cargen ST-60", trade name; surfactant) | 8% |

COMPARATIVE EXAMPLE 17

| | |
|---|---|
| Propanil | 35% |
| Diethylene glycol mono-2-ethylhexyl ether | 32% |
| Dimethylsulfoxide | 25% |
| Mixture of polyoxyalkylene arylphenyl ether and alkyl benzene sulfonate ("New Cargen ST-60", trade name; surfactant) | 8% |

COMPARATIVE EXAMPLE 18

| | |
|---|---|
| Propanil | 35% |
| Diethylene glycol mono-2-ethylhexyl ether | 12% |
| Dimethylsulfoxide | 25% |
| Xylene | 20% |
| Mixture of polyoxyalkylene arylphenyl ether and alkyl benzene sulfonate ("New Cargen ST-60", trade name; surfactant) | 8% |

COMPARATIVE EXAMPLE 19

| | |
|---|---|
| Propanil | 35% |
| Diethylene glycol mono-2-ethylhexyl ether | 27% |
| Dimethylsulfoxide | 5% |

-continued

| | |
|---|---|
| Xylene | 25% |
| Mixture of polyoxyalkylene arylphenyl ether and alkyl benzene sulfonate ("New Cargen ST-60", trade name; surfactant) | 8% |

Test 1 ("Storage Stability" Test)

The composition in the form of the solution or emulsifiable concentrated solution propanil, which had been prepared in each of some of the Examples or Comparative Examples as above, was placed in a 100-ml glass bottle, to which an very small amount of propanil crystals was added as seed crystals. After the composition was stored for 30 days at $-5°$ C. or $-20°$ C., occurrence of the precipitation of propanil solids or crystals and any changes in external appearance of the composition tested were observed. Further, after storage for 30 days at $-5°$ C. or $-20°$ C., the composition was allowed to stand for one day at room temperature (20° C.), occurrence of the precipitation of propanil solids or crystals and any changes in external appearance of the composition tested were similarly observed. The test results are expressed by the following evaluation symbols:

a: No objectionable change such as precipitation or crystallization of propanil was observed;

c: Significant precipitation of propanil solids or crystals was observed in the tested composition in the form of the solution or emulsifiable concentrated solution of propanil.

The concrete formulations (the constituents present in) of the compositions as tested here of the Examples and Comparative Examples are tabulated in Tables 1A to Table 4A hereinafter, and the test results obtained with these compositions are summarized in Tables 1B to Table 4B hereinafter.

Test 2 ("Emulsion Stability" Test)

Two portions of the composition in the form of the emulsifiable concentrated solution of propanil, which were prepared in each of some Examples or Comparative Examples as above, was mixed and diluted 100-fold with water at 20° C. and 5° C., respectively, for preparation of the aqueous emulsions, whereby 100-fold dilutions were obtained. One liter of each of the resulting aqueous emulsions as formed by dilution with water was allowed to stand for 2 hours at the corresponding temperature at 20° C. or at 5° C. and then passed through a 300-mesh screen. The presence or absence of propanil solids or crystals remaining on the screen was observed. Further, using a magnetic stirrer, another one liter of each of the said resulting aqueous emulsions was stirred for 2 hours at the rate of 200 rpm with a stirring rod of 5 cm long. Each of the aqueous emulsions stirred was then allowed to stand for 2 hours, at 20° C. or at 5° C., and presence absence of propanil solids or crystals precipitated in the tested emulsion was similarly observed.

Similar tests were conducted also with respect to the aqueous emulsions which were obtained by mixing and diluting the composition in the form of the emulsifiable concentrated solution of propanil with water to a 300-fold dilution. The test results are expressed by the following evaluation symbols:

a: Precipitation or crystallization of propanil was not observed.

b: Precipitation or crystallization of a very small or trace amount of propanil was observed.

c: Precipitation or crystallization of a large amount of propanil was observed.

The concrete formulations (the constituents present in) of the compositions as tested here of the Examples and Comparative Examples are tabulated in Tables 1A to 4A hereinafter, and the test results obtained here with these compositions are again summarized in Tables 2B and 4B hereinafter.

TABLE 1A

Constituents in the tested Compositions in the form of Solutions of Propanil in Solvent

| Composition | Propanil (wt. %) | Solvent A (wt. %) | Solvent B (wt. %) | Weight ratio Solvent A to Solvent B |
|---|---|---|---|---|
| Example 1 | 35 | DEG-MEHE(60) | DMSO(5) | 1:0.083 |
| Example 2 | 35 | EG-MHE(55) | MPD(10) | 1:0.182 |
| Comp. Ex. 1 | 35 | DEG-MEHE(65) | | |
| Comp. Ex. 2 | 35 | EG-MHE65) | | |

Note: Solvent A = glycol ether-type solvent
Solvent B = dimethylsulfoxide (DMSO) or N-methyl-2-pyrrolidone (MPD)
DEG-MEHE = diethylene glycol mono-2-ethylhexyl ether
EG-MHE = ethylene glycol monohexyl ether

TABLE 1B

"Storage Stability" Test for Compositions in the form of Solutions of Propanil in Solvents

| | Storage stability test Storage conditions for tests | | | |
|---|---|---|---|---|
| Composition | $-5°$ C., 30 days | $-20°$ C., 30 days | $-5°$ C., 30 days, then 20° C., 1 day | $-20°$ C., 30 days, then 20° C., 1 day |
| Example 1 | a | a | a | a |
| Example 2 | a | a | a | a |
| Comp. Ex. 1 | c | c | c | c |
| Comp. Ex. 2 | c | c | c | c |

TABLE 2A

Constituents in the tested Compositions in the form of Emulsifiable Concentrated solutions of Propanil

| Composition | Propanil (wt. %) | Solvent A (wt. %) | Solvent B (wt. %) | Solvent C (wt. %) | Surfactant (wt. %) | Weight ratio of Solvent A to Solvent B | Proportion of Solvent C (wt. %, in A + B + C) |
|---|---|---|---|---|---|---|---|
| Example 3 | 35 | DEG-MEHE (52) | DMSO (5) | | 8 | 1:0.096 | |
| Example 4 | 35 | DEG-MEHE (37) | DMSO (5) | Xylene (15) | 8 | 1:0.135 | 26 |
| Example 5 | 35 | EG-MHE (45) | MPD (10) | | 10 | 1:0.222 | |
| Example 6 | 35 | EG-MHE (35) | MPD (10) | methylnaphthalene (10) | 10 | 1:0.286 | 18 |
| Example 7 | 45 | DEG-DBE (35) | MPD (15) | | 5 | 1:0.429 | |
| Example 8 | 10 | EG-MPE (75) | DMSO (5) | | 10 | 1:0.067 | |
| Example 9 | 35 | EG-MEHE (37) | DMSO (5) | Xylene (5) | 8 | 1:0.135 | 26 |
| Comp. Ex. 3 | 35 | DEG-MEHE (57) | | | 8 | | |
| Comp. Ex. 4 | 35 | | DMSO (57) | | 8 | | |
| Comp. Ex. 5 | 35 | | DMSO (5) | Xylene (52) | 8 | | |

TABLE 2A-continued

Constituents in the tested Compositions in the form of Emulsifiable Concentrated solutions of Propanil

| Composition | Propanil (wt. %) | Solvent A (wt. %) | Solvent B (wt. %) | Solvent C (wt. %) | Surfactant (wt. %) | Weight ratio of Solvent A to Solvent B | Proportion of Solvent C (wt. %, in A + B + C) |
|---|---|---|---|---|---|---|---|
| Comp. Ex. 6 | 35 | DEG-MEHE (52) | *DMF (5) | | 8 | 1:0.096 | |
| Comp. Ex. 7 | 35 | DEG-MEHE (42) | | Xylene (15) | 8 | | |
| Comp. Ex. 8 | 35 | *EG-DEE (37) | DMSO (5) | Xylene (15) | 8 | 1:0.135 | 26 |
| Comp. Ex. 9 | 35 | EG-MHE (55) | | | 10 | | |
| Comp. Ex. 10 | 35 | | MPD (55) | | 10 | | |
| Comp. Ex. 11 | 35 | | MPD (10) | methylnaphthalene (45) | 10 | | |
| Comp. Ex. 12 | 35 | EG-MHE (45) | *PrOH (10) | | 10 | 1:0.222 | |
| Comp. Ex. 13 | 35 | EG-MHE (45) | | methylnaphthalene (10) | 10 | | |
| Comp. Ex. 14 | 35 | | *CHN (38) | Xylene (7) | 20 | | |
| Comp. Ex. 15 | 35 | | *MHK (40) | Xylene (10) | 15 | | |
| Comp. Ex. 16 | 35 | | *isophorone (30) | Xylene (25) | 10 | | | note:
Solvent A = glycol ether-type solvent
Solvent B = dimethylsulfoxide (DMSO) or N-methyl-2-pyrrolidone (MPD)
Solvent C = aromatic solvent
DEG-MEHE = diethylene glycol mono-2-ethylhexyl ether
EG-MHE = ethylene glycol monohexyl ether
DEG-DBE = diethylene glycol dibutyl ether
EG-MPE = ethylene glycol monophenyl ether
EG-MEHE =0 ethylene glycol mono-2-ethylhexyl ether
*EG-DEE = ethylene glycol diethyl ether
*DMF = dimethyl formamide
*CHN = cyclohexanone
*PrOH = n-propyl alcohol
*MHK = methyl n-hexyl ketone
*Solvent other than those used in the present inventions

TABLE 2B

"Storage Stability" and "Emulsion Stability" Tests for Compositions in the form of Emusifiable Concentrated Solution of Propanil

| | Storage stability test | | | | Emulsion stability test | | | | | | | |
|---|---|---|---|---|---|---|---|---|---|---|---|---|
| | Storage conditions for Tests | | | | Test conditions | | | | | | | |
| | | | | | Allowed to stand | | | | Allowed to stand after stirring | | | |
| | | | −5° C., 30 days then | −20° C., 30 days, then | At 100-fold Dilution | | At 300-fold Dilution | | At 100-fold Dilution | | At 300-fold Dilution | |
| Composition | −5° C., 30 days | −20° C., 30 days | 20° C., 1 day | 20° C., 1 day | Temp. 20° C. | Temp. 5° C. | Temp. 20° C. | Temp. 5° C. | Temp. 20° C. | Temp. 5° C. | Temp. 20° C. | Temp. 5° C. |
| Example 3 | a | a | a | a | a | a | a | a | a | a | a | b |
| Example 4 | a | a | a | a | a | a | a | a | a | a | a | a |
| Example 5 | a | a | a | a | a | a | a | a | a | a | a | b |
| Example 6 | a | a | a | a | a | a | a | a | a | a | a | a |
| Example 7 | a | a | a | a | a | a | a | a | a | a | a | a |
| Example 8 | a | a | a | a | a | a | a | a | a | a | a | b |
| Example 9 | a | a | a | a | a | a | a | a | a | a | a | a |
| Comp. Ex. 3 | c | c | c | c | a | a | a | a | a | a | a | b |
| Comp. Ex. 4 | a | c | a | a | c | c | c | c | c | c | c | c |
| Comp. Ex. 5 | c | c | c | c | c | c | c | c | c | c | c | c |
| Comp. Ex. 6 | a | c | a | c | a | a | a | a | a | a | a | b |
| Comp. Ex. 7 | c | c | c | c | a | a | a | a | a | a | a | a |
| Comp. Ex. 8 | a | a | a | a | c | c | c | c | c | c | c | c |
| Comp. Ex. 9 | c | c | c | c | a | a | a | a | a | a | a | b |
| Comp. Ex. 10 | a | a | a | a | c | c | c | c | c | c | c | c |
| Comp. Ex. 11 | a | c | a | c | a | c | a | c | c | c | c | c |
| Comp. Ex. 12 | a | c | a | c | a | a | a | a | a | a | a | b |
| Comp. Ex. 13 | c | c | c | c | a | a | a | a | a | a | a | a |
| Comp. Ex. 14 | a | a | a | a | a | a | a | a | a | c | a | c |
| Comp. Ex. 15 | a | c | a | c | a | a | a | a | a | a | a | b |
| Comp. Ex. 16 | a | c | a | c | a | a | a | a | a | b | a | c |

As is shown in Table 2B, the composition according to this invention are superior both in storage stability and emulsion stability.

TABLE 3A

Constituents in the tested Compositions in the form of Solutions of Propanil

| Composition | Propanil (wt. %) | Solvent A (wt. %) | Solvent B (wt. %) | Solvent C (wt. %) | Weight ratio of Solvent A to Solvent B | Proportion of Solvent C (wt. %, in A + B + C) |
|---|---|---|---|---|---|---|
| Example 10 | 35 | EG-MHE (55) | DMSO + MPD (5 + 5) | | 1:0.182 | |
| Example 11 | 10 | DEG-MEHE (85) | DMSO (5) | | 1:0.059 | |
| Example 12 | 14 | DEG-MEHE (85) | DMSO (1) | | 1:0.012 | |

TABLE 3A-continued

Constituents in the tested Compositions in the form of Solutions of Propanil

| Composition | Propanil (wt. %) | Solvent A (wt. %) | Solvent B (wt. %) | Solvent C (wt. %) | Weight ratio of Solvent A to Solvent B | Proportion of Solvent C (wt. %, in A + B + C) |
|---|---|---|---|---|---|---|
| Example 13 | 45 | DEG-MEHE (35) | DMSO (20) | | 1:0.571 | |
| Example 14 | 35 | DEG-MEHE (45) | DMSO (5) | Xylene (15) | 1:0.111 | 23 | note:
Solvent A = glycol ether-type solvent
Solvent B = dimethylsulfoxide (DMSO) or N-methyl-2-pyrrolidone (MPD)
Solvent C = 0 aromatic solvent
EG-MHE = ethylene glycol monohexyl ether
DEG-MEHE = diethylene glycol mono-2-ethylhexyl ether

TABLE 3B

"Storage Stability" Test for Compositions in the form of Solutions of Propanil in Solvents

| Composition | Storage stability test Storage conditions for tests | | | |
|---|---|---|---|---|
| | −5° C., 30 days | −20° C., 30 days | −5° C., 30 days, then 20° C., 1 day | −20° C., 30 days, then 20° C., 1 day |
| Example 10 | a | a | a | a |
| Example 11 | a | a | a | a |
| Example 12 | a | a | a | a |
| Example 13 | a | a | a | a |
| Example 14 | a | a | a | a |

TABLE 4A

Constituents in the tested Compositions in the form of Emulsifiable Concentrated Solutions of Propanil

| Composition | Propanil (Wt. %) | Solvent A (wt. %) | Solvent B (wt. %) | Solvent C (wt. %) | Surfactant (wt. %) | Weight ratio of Solvent A to Solvent B | Proportion of Solvent C (wt. %, in A + B + C) |
|---|---|---|---|---|---|---|---|
| Example 28 | 35 | EG-MHE (45) | DMSO + MPD (5 + 5) | | 10 | 1:0.222 | |
| Example 29 | 10 | DEG-MEHE (85) | DMSO (1) | | 4 | 1:0.012 | |
| Example 30 | 45 | DEG-MEHE (39) | DMSO (1) | | 15 | 1:0.026 | |
| Example 31 | 45 | DEG-MEHE (20) | DMSO (20) | | 15 | 1:1.000 | |
| Example 32 | 10 | DEG-MEHE (82) | DMSO (1) | Xylene (5) | 2 | 1:0.012 | 6 |
| Example 33 | 30 | DEG-MEHE (20) | DMSO (20) | Xylene (20) | 10 | 1:1.000 | 33 |
| Example 34 | 45 | DEG-MEHE (20) | DMSO (20) | Xylene (5) | 10 | 1:1.000 | 11 |
| Comp. Ex. 17 | 35 | DEG-MEHE (32) | DMSO (25) | | 8 | 1:0.781 | |
| Comp. Ex. 18 | 35 | DEG-MEHE (12) | DMSO (25) | Xylene (20) | 8 | 1:2.083 | 35 |
| Comp. Ex. 19 | 35 | DEG-MEHE (27) | DMSO (5) | Xylene (25) | 8 | 1:0.185 | 44 | note:
Solvent A = glycol ether-type solvent
Solvent B = dimethylsulfoxide (DMSO) or N-methyl-2-pyrrolidone (MPD)
Solvent C = aromatic solvent
EG-MHE = ethylene glycol monohexyl ether
DEG-MEHE = diethylene glycol mono-2-ethylhexyl ether

TABLE 4B

"Storage Stability" and "Emulsion Stability" Tests for compositions in the form of Emusifiable Concentrated Solution of Propanil

| Composition | Storage stability test Storage conditions for Tests | | | | Emulsion stability test Test conditions | | | | | | | |
|---|---|---|---|---|---|---|---|---|---|---|---|---|
| | | | | | Allowed to stand | | | | Allowed to stand after stirring | | | |
| | | | | | At 100-fold Dilution | | At 300-fold Dilution | | At 100-fold Dilution | | At 300-fold Dilution | |
| | −5° C., 30 days | −20° C., 30 days | −5° C., 30 days then 20° C., 1 day | −20° C., 30 days, then 20° C., 1 day | Temp. 20° C. | Temp. 5° C. | Temp. 20° C. | Temp. 5° C. | Temp. 20° C. | Temp. 5° C. | Temp. 20° C. | Temp. 5° C. |
| Example 28 | a | a | a | a | a | a | a | a | a | a | a | b |
| Example 29 | a | a | a | a | a | a | a | a | a | a | a | b |
| Example 30 | a | a | a | a | a | a | a | a | a | a | a | b |
| Example 31 | a | a | a | a | a | a | a | a | a | a | a | b |
| Example 32 | a | a | a | a | a | a | a | a | a | a | a | a |
| Example 33 | a | a | a | a | a | a | a | a | a | a | a | a |
| Example 34 | a | a | a | a | a | a | a | a | a | a | a | a |
| Comp. Ex. 17 | c | c | c | c | a | a | a | a | a | a | a | b |
| Comp. Ex. 18 | a | c | a | a | c | c | c | c | c | c | c | c |
| Comp. Ex. 19 | c | c | c | c | c | c | c | c | c | c | c | c |

As is shown in Table 4B, the composition according to this invention are superior both in storage stability and emulsion stability.

With the compositions in the form of a solution of propanil according to Examples 15 to 27 and the compositions in the form of an emulsifiable concentrated solution of propanil according to Examples 35 to 45, the test results obtained therefor were similar to the test results given in the Tables 1B, 2B, 3B and 4B but are not given in Table 1B to Table 4B.

We claim:

1. A herbicide composition in the form of a stable solution of propanil, namely N-(3,4-dichlorophenyl)-propionamide as a herbicidally active ingredient dissolved in solvent, said composition having no or little tendency to precipitate or crystallize propanil as solids from the solution upon storage even in a cold place, wherein the solvent used is a solvent mixture consisting essentially of (a) a solvent of the glycol ether-type having a solubility of not more than 5% by weight in water at 20° C., (b) dimethylsulfoxide or (c) N-methyl-2-pyrrolidone and (d) an aromatic solvent, and wherein propanil is present in an amount of 10 to 45% by weight, especially 30 to 45% by weight, (a) the glycol ether-type solvent is present in an amount of 20 to 85% by weight, (b) dimethylsulfoxide or (c) N-methyl-2-pyrrolidone is present in an amount of 1 to 20% by weight and (d) the aromatic solvent is present in an amount of 5 to 20% by weight, on the basis of the total weight of the composition.

2. A composition as claimed in claim 1, wherein the weight ratio between the glycol ether-type solvent and dimethylsulfoxide or N-methyl-2-pyrrolidone present in the solvent mixture consisting essentially of the glycol ether-type solvent, dimethylsulfoxide or N-methyl-2-pyrrolidone and the aromatic solvent is in a range of 1:1 to 1:0.01, and said solvent mixture contains the aromatic solvent in a proportion of 5 to 44% by weight based on the total weight of said solvent mixture.

3. A composition as claimed in claim 1, wherein the glycol ether-type solvent is of the formula (1):

$$R_1-(O-R_2)_n-OH \quad (1)$$

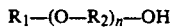

in which $R_1$ and $R_2$ individually represent an alkyl group having 5 to 9 carbon atoms, or phenyl group and n represents an integer of 1 to 2.

4. A composition as claimed in claim 1, wherein the glycol ether-type solvent is of the formula (2):

$$R_3-O-(R_4-O)_m-R_5 \quad (2)$$

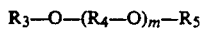

in which $R_3$, $R_4$ and $R_5$ individually represent an alkyl group having 3 to 5 carbon atoms and m represents an integer 1 to 2.

5. A composition as claimed in claim 1, wherein the glycol ether-type solvent is selected from ethylene glycol monohexyl ether, diethylene glycol monohexyl ether, ethylene glycol mono-2-ethylhexyl ether, diethylene glycol mono-2-ethylhexyl ether, ethylene glycol monophenyl ether, propylene glycol monophenyl ether and dipropylene glycol monopropyl ether, as well as ethylene glycol dibutyl ether and diethylene glycol dibutyl ether.

6. A composition as claimed in claim 1, wherein the aromatic solvent is selected from xylene, methylnaphthalene' solvent naphtha, ethylbenzene, chlorobenzene and dichlorobenzene.

7. A herbicide composition in the form of a stable emulsifiable concentrated solution containing propanil as a herbicidally active ingredient dissolved in solvent together with at least one surface active agent, said composition having no or little tendency to precipitate or crystallize propanil as solids from the aqueous emulsion formed upon dilution of said solution with water and upon storage of said solution, wherein the solvent used is a solvent mixture consisting essentially of (a) such a solvent of the glycol ether-type having a solubility of not more than 5% by weight in water at 20° C., (b) dimethylsulfoxide or (c) N-methyl-2-pyrrolidone and (d) an aromatic solvent, and wherein propanil is present in an amount of 20 to 85% by weight, (b) dimethylsulfoxide or (c) N-methyl-2-pyrrolidone is present in an amount of 1 to 20% by weight and (d) the aromatic solvent is present in an amount of 5 to 20% by weight, on the basis of the total weight of the composition.

8. A composition as claimed in claim 7, wherein the weight ratio between the glycol ether-type solvent and dimethylsulfoxide or N-methyl-2-pyrrolidone present in the solvent mixture consisting essentially of the glycol ether-type solvent, dimethylsulfoxide or N-methyl-2-pyrrolidone and the aromatic solvent is in a range of 1:1 to 1:0.01, and said solvent mixture contains the aromatic solvent in a proportion of 5 to 35% by weight based on the total weight of said solvent mixture and wherein the surface active agent or agents is or are present in an amount of 2 to 15% by weight on the basis of the total weight of the composition.

9. A composition as claimed in claim 7, wherein the $$R_1-(O-R_2)_n-OH \quad (1)$$

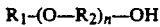

in which $R_1$ and $R_2$ individually represent an alkyl group having 5 to 9 carbon atoms, or phenyl group and n represents an integer of 1 to 2.

10. A composition as claimed in claim 7, wherein the glycol ether-type solvent is of the formula (2):

$$R_3-O-(R_4-O)_m-R_5 \quad (2)$$

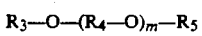

in which $R_3$, $R_4$ and $R_5$ individually represent an alkyl group having 3 to 5 carbon atoms and m represents an integer of 1 to 2.

11. A composition as claimed in 7, wherein the glycol ether-type solvent is selected from ethylene glycol monohexyl ether, diethylene glycol monohexyl ether, ethylene glycol mono-2-ethylhexyl ether, diethylene glycol mono-2-ethylhexyl ether, ethylene glycol monophenyl ether, propylene glycol monophenyl ether and dipropylene glycol monopropyl ether, as well as ethylene glycol dibutyl ether and diethylene glycol dibutyl ether.

12. A composition as claimed in claim 7, wherein the aromatic solvent is selected from xylene, methylnaphthalene, solvent naphtha, ethylbenzene, chlorobenzene and dichlorobenzene.

13. A herbicide composition in the form of a stable solution of propanil as a herbicidally active ingredient dissolved in solvent, said composition having nor or little tendency to precipitate or crystallize propanil as solids from the solution upon storage even in cold place, wherein the solvent used is a solvent mixture consisting essentially of (a) such a solvent of the glycol ether-type having a solubility of not more than 5% by weight in water at 20° C, (b) dimethylsulfoxide and (c) N-methyl-2-pyrrolidone, as well as (d) an aromatic solvent, and wherein propanil is present in an amount of 10 to 45% by weight, especially 30 to 45% by weight, (a) the glycol ether-type solvent is present in an amount of 20 to 85% by weight, (b) dimethylsulfoxide and (c) N-methyl-2-pyrrolidone are totally present in an amount of 1 to 20% by weight and (d) the aromatic solvent is present in an amount of 5 to 20% by weight, on the basis of the total weight of the composition.

14. A herbicide composition in the form of a stable emulsifiable concentrated solution containing propanil as a herbicidally active ingredient dissolved in solvent together with at least one surface active agent, said composition having no or little tendency to precipitate or crystallize propanil as solids from the aqueous emulsion formed upon dilution of said solution with water and upon storage of said solution, wherein the solvent used is a solvent mixture consisting essentially of (a) such a solvent of the glycol ether-type having a solubility of not more than 5% by weight in water at 20° C., (b) dimethylsulfoxide and (c) N-methyl-2-pyrrolidone as well as (d) an aromatic solvent, and wherein propanil is present in an amount of 10 to 45% by weight, especially 30 to 45% by weight, (a) the glycol ether-type solvent is present in an amount of 20 to 85% by weight, (b) dimethylsulfoxide and (c) N-methyl-2-pyrrolidone are totally present in an amount of 1 to 20% by weight, and (d) the aromatic solvent is present in an amount of 5 to 20% by weight, on the basis of the total weight of the composition, and wherein the surface active agent or agents is or are present in an amount of 2 to 15% by weight of the total weight of the composition.

* * * * *

UNITED STATES PATENT AND TRADEMARK OFFICE
CERTIFICATE OF CORRECTION

PATENT NO.  : 5,273,955
DATED       : December 28, 1993
INVENTOR(S) : FUJITA, et al.

It is certified that error appears in the above-identified patent and that said Letters Patent is hereby corrected as shown below:

Column 28, line 10, before "20 to 85%", insert

-- 10 to 45% by weight, especially 30 to 45% by weight, (a) glycol ether-type solvent is present in an amount of --

Signed and Sealed this

Twenty-third Day of May, 1995

Attest:

BRUCE LEHMAN

*Attesting Officer*    Commissioner of Patents and Trademarks